United States Patent
Shrivastava

(10) Patent No.: US 8,192,554 B2
(45) Date of Patent: *Jun. 5, 2012

(54) METHOD OF DESCALING METALLIC DEVICES

(75) Inventor: Sanjay Shrivastava, Irvine, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/232,178

(22) Filed: Sep. 14, 2011

(65) Prior Publication Data

US 2012/0000791 A1    Jan. 5, 2012

Related U.S. Application Data

(63) Continuation of application No. 11/370,660, filed on Mar. 7, 2006, now Pat. No. 8,038,803.

(51) Int. Cl.
*B08B 3/00* (2006.01)
*B08B 3/10* (2006.01)
*C23G 1/00* (2006.01)

(52) U.S. Cl. .......... 134/26; 134/2; 134/3; 134/25.1; 134/25.4; 134/28; 134/29; 134/42

(58) Field of Classification Search .......... 134/2, 3, 134/25.1, 25.4, 26, 28, 29, 42
See application file for complete search history.

(56) References Cited

U.S. PATENT DOCUMENTS

| | | | | |
|---|---|---|---|---|
| 2,430,951 A | * | 11/1947 | Rouault | 508/527 |
| 3,835,082 A | * | 9/1974 | Wright | 524/510 |
| 4,314,876 A | * | 2/1982 | Kremer et al. | 216/109 |
| 5,286,300 A | * | 2/1994 | Hnatin et al. | 134/2 |
| 5,350,419 A | | 9/1994 | Bendel et al. | |
| 5,759,102 A | | 6/1998 | Pease et al. | |
| 5,759,192 A | | 6/1998 | Saunders | |
| 5,858,556 A | | 1/1999 | Eckert et al. | |
| 6,117,485 A | * | 9/2000 | Woodhall et al. | 427/156 |
| 6,537,459 B1 | * | 3/2003 | Dufresne et al. | 216/8 |
| 6,632,291 B2 | | 10/2003 | Rabon et al. | |
| 6,679,980 B1 | * | 1/2004 | Andreacchi | 204/272 |
| 6,960,370 B2 | | 11/2005 | Monni et al. | |
| 2004/0188261 A1 | | 9/2004 | Monni et al. | |
| 2005/0131522 A1 | | 6/2005 | Stinson et al. | |
| 2007/0209685 A1 | | 9/2007 | Shrivastava | |

OTHER PUBLICATIONS

McLaughlin et al., The Aqueous Cleaning Handbook. AL Technial Communications. 3$^{rd}$ Ed. 2002. pp. 22, 29 and 32.*
"The Aqueous Cleaning Handbook", A Guide to Critical-Cleaning Procedures, techniques, and validation, 3rd Edition, Malcolmm C. McLaughlin, M.A., Alan S. Zisman, M.D. & Staff, 2002.
Definition of scale. Acquired Jun. 2, 2008 from Dictionary.com, p. 2.
U.S. Appl. No. 11/370,660, Nov. 27, 2007, Office Action.
U.S. Appl. No. 11/370,660, Jun. 9, 2008, Office Action.
U.S. Appl. No. 11/370,660, Jan. 13, 2009, Office Action.
U.S. Appl. No. 11/370,660, Aug. 27, 2009, Office Action.
U.S. Appl. No. 11/370,660, May 25, 2010, Office Action.
U.S. Appl. No. 11/370,660, Sep. 3, 2010, Office Action.
U.S. Appl. No. 11/370,660, Mar. 21, 2011, Office Action.
U.S. Appl. No. 11/370,660, Jun. 23, 2011, Notice of Allowance.
U.S. Appl. No. 11/370,660, Sep. 28, 2011, Issue Notification.

* cited by examiner

*Primary Examiner* — Michael Kornakov
*Assistant Examiner* — Nicole Blan
(74) *Attorney, Agent, or Firm* — Workman Nydegger; John Kwok

(57) ABSTRACT

Methods are provided for descaling metallic component devices such as stents. The devices or components are cleaned under ultrasound in a cleaning solution of ammonium hydrogen fluoride at a temperature within a range of about 60° to 80° C., then rinsed at that temperature with an aqueous rinse containing a nonionic surfactant and rinsed again with purified water.

24 Claims, No Drawings

METHOD OF DESCALING METALLIC DEVICES

CROSS-REFERENCE TO RELATED APPLICATIONS

This application is a continuation of U.S. patent application Ser. No. 11/370,660 filed Mar. 7, 2006, now U.S. Pat. No. 8,038,803 which is incorporated herein by reference in its entirety.

BACKGROUND

The present invention relates generally to methods for descaling devices or components made from metals, and in particular, metallic stents. The methods are particularly directed to the descaling of medical devices made of titanium, stainless steel, tungsten, nickel-titanium, tantalum, cobalt-chromium-tungsten, or cobalt-chromium. While the devices and components to which the present methods are applicable are described mainly as stents, in particular intravascular stents, the invention is not limited to such medical products or stents. For example, the methods may be applied to descale metallic automotive or aerospace structural components.

Stents are generally tube-shaped intravascular devices placed within a blood vessel to maintain the potency of the vessel and, in some cases, to reduce the development of restenosis. The stents may be formed in a variety of configurations which are typically expandable since they are delivered in a compressed form to the desired site. Such a configuration may be a helically wound wire, wire mesh, weaved wire, serpentine stent, or a chain of rings. The walls of stents are typically perforated in a framework design of wire-like connected elements or struts or in a weave design of cross-threaded wire. Some stents are made of more than one material. The stent may be, for example, a sandwich of metals having outer layers of a biocompatible material, such as stainless steel, with an inner layer providing the radiopacity to the stent needed for tracking by imaging devices during placement. A stent made of such material may be, for example, a thin layer of titanium between two layers of stainless steel. In forming such stents from metal, a roughened outer surface of the stent may result from the manufacturing process. It is desirable for the surface of the stent to be smooth so that it can be easily inserted and traversed with low friction through the blood vessels toward the site of implantation. A rough outer surface may not only cause increased frictional obstruction, but may also damage the lining of the vessel wall during insertion. Furthermore, smooth surfaces decrease the probability of thrombogenesis and corrosion.

Since the processing to form metallic stents often results in a product initially having undesirable burrs, sharp ends or debris and slag material from melting the metal during processing, as a first order treatment of the product, descaling of the surface is required in preparation of further surface treatment such as electropolishing.

The present invention provides methods for descaling metallic devices and components, in particular, metallic medical stents.

BRIEF SUMMARY

The invention is directed to a method of descaling a metallic device or component, such as a stent, comprising:
a) placing the device or component in contact with a solution of ammonium hydrogen fluoride at a temperature in the range of about 60° to 80° C. for a period of time sufficient to descale the device or component while applying ultrasonic energy to the solution;
b) removing the device or component from the solution and contacting it with a first aqueous rinse containing a nonionic surfactant at a temperature in the range of about 60° to 80° C. while applying ultrasonic energy to the first rinse;
c) removing the device or component from the first rinse and contacting it with a second aqueous rinse while applying ultrasonic energy to the second rinse; and
d) optionally, removing the device or component from the second rinse and immersing it in a non-corrosive liquid.

In one embodiment the temperature ranges in steps a) and b) are about 65° to 75° C.

In one embodiment, step c) is conducted within the temperature range of about 60° to 80° C. In another embodiment, step c) is conducted within a temperature range of about 65° to 75° C.

In another embodiment, the concentration of ammonium hydrogen fluoride in the solution is about 3 to 6 percent by volume.

Other features of the invention will become apparent from the following detailed description.

DETAILED DESCRIPTION

The present invention is directed to a method for descaling metallic devices or components, in particular, metallic stents. By descaling it is meant to remove undesirable burrs, nicks, sharp ends or debris and slag material attached to the stent.

The invention is described in connection with an embodiment of descaling a single stent, but it is preferred that the stents be descaled in batches. A typical batch will contain three to seven stents, typically five stents having relatively similar lengths.

Since hazardous materials are used in the method of the invention, it would typically be conducted under a ventilated fume hood with the users using suitable protective clothing.

The primary descaling solution is an ammonium hydrogen fluoride (AHF) solution, $NH_4F.HF$, prepared by mixing ammonium difluoride with about 30% nitric acid. Typically about six ounces of ammonium difluoride is used per gallon of 30% nitric acid. Typically the concentration of ammonium hydrogen fluoride will be in a range of about 4 to 6% by volume in the solution. This solution is typically prepared in advance and warmed to a suitable temperature in the range of about 60° to 80° C. Particularly suitable temperatures are in the range of about 65° to 75° C.

The AHF solution is advantageous because it dissolves metals commonly used in metallic medical devices at approximately the same rate. In the case of multilayered composites of different metals the exposed ends of the composite may comprise several different and distinct metal edges. If these metals are not dissolved at approximately the same rate in the cleaning solution, the slower-dissolving metals will form protrusions as the surrounding faster-dissolving metals dissolve. These protrusions are also defects. To avoid this, the cleaning solution must be sufficient to attack commonly used metals, such as stainless steel, tantalum and titanium, at approximately the same rate.

A first aqueous rinse is prepared containing a nonionic surfactant, such as Triton® X-100. Triton® X-100 comprises a polyoxyethylene octyl phenyl ether of the formula $C_{14}H_{22}O(C_2H_4O)_n$ where the average n per molecule is about 9 or 10. Liquinox® is another suitable nonionic surfactant. It comprises sodium dodecylbenzenesulfonate, typically used at a concentration of about 1% by volume in the first aqueous rinse. The first aqueous rinse will comprise purified water and the nonionic surfactant. Typically a small amount of the surfactant is sufficient, usually in the range of about 0.2 to 1% by volume. A useful concentration is about 0.4% of nonionic surfactant by volume in the purified water.

The method according to the present invention includes the following steps. First, the ammonium hydrogen fluoride (AHF) solution is prepared and brought to the required temperature. A useful working temperature is about 70° C. This is preferably accomplished by partially immersing the vessel containing the solution in a bath. Ultrasonic energy is applied to the bath, preferably during its warm-up period and remains applied during the cleaning stage. Then the stent or batch of stents is immersed into the AHF solution for a period of time sufficient to descale the stent or stents. Depending on the size of the stents and the number of stents in the batch, this period of time may vary from several minutes to 30 minutes or more. In a typical batch of five stents each having a length of about 8 to 15 millimeters, the cleaning time in the AHF solution will be about 7 minutes. If the batch of five contains stents having a length in the range of about 18 to 28 millimeters, the cleaning time will be about 10 minutes. The typical cleaning solution of AHF for metallic stents needs only to be a volume of around 25 to 50 milliliters.

After the desired cleaning period in the cleaning solution has expired, the stents are removed and inserted into the first aqueous rinse containing the nonionic surfactant. This first aqueous rinse should also be at a temperature within a range of about 60° to 80° C., typically about 65° to 75° C. The usual temperature of this rinse will be about 70° C., the same temperature used for the cleaning solution. To rinse a typical batch of about five stents, this first aqueous rinse need only have a volume of about 60 milliliters. Typically the stents will remain in the first aqueous rinse for about 3 to 5 minutes while applying ultrasonic energy to the rinse. For a typical batch of about 5 stents, the stents will remain within the rinse for about 3¾ to 4¼ minutes.

After the first rinse, the stents are then placed into the second aqueous rinse, which is purified water, during which ultrasonic energy is also applied to the rinse. The purified water is also typically between temperatures between about 60° to 80° C., more usually about 65° to 75° C. Preferably the temperature of 70° C. is used, the same temperature used for the first aqueous rinse and the cleaning solution. Typically the stents remain in the second aqueous rinse also for about 3¾ to 4¼ minutes. The volume of the first aqueous rinse for using typical batches of five stents is about 60 mls. The volume of the second aqueous rinse for typical batches of five stents is about 30 mls.

After the second aqueous rinse, the stents are then ready for electro polishing. They may be electropolished immediately or stored for later processing. Typically the stents will be stored in alcohol or other suitable non-corrosive liquid to prevent corrosion.

The following example is provided for purpose of illustration and is not intended to limit the invention in any way.

EXAMPLE

A 4.5 percent by volume solution of ammonium hydrogen fluoride solution (AHF) is prepared by adding 6 oz. of ammonium difluoride to a gallon of 30 percent nitric acid. A 25 ml portion of this solution is placed in a PTFE beaker and placed in an ultrasonic bath. The ultrasound is turned on and set for 20 minutes while the AHF solution is warmed. After approximately 10 minutes, the temperature is checked by a thermocouple probe, and the temperature is checked in approximately one-minute intervals until the solution reaches 70° C. Triplex stents are fabricated having a thin layer of titanium sandwiched between two layers of stainless steel, typically having a total strut thickness of about 0.003 mm. For a batch of five stents (having a length and range of 8 to 15 millimeters) the cleaning time will be about 7 minutes at 70° C. For a batch of five stents having a length in the range of about 18 to 28 millimeters, the cleaning time will be about 10 minutes at 70° C. With about 2 to 3 minutes remaining on the ultrasound timer, a glass beaker containing 60.25 mls of the first aqueous rinse is inserted into the ultrasound bath. This rinse is prepared by dispensing 60 ml of purified water into a glass beaker and adding 5 drops of Triton® X-100 nonionic surfactant (about 0.25 ml). The rinse is allowed to reach 70° C. in the bath. Once the AHF cleaning time has elapsed, the stents are promptly removed from the AHF solution and transferred to the first aqueous rinse where they remain for about 4 minutes. Rinse time is typically about 3¾ to 4¼ minutes, while the first aqueous rinse is in the temperature range of about 65° to 75° C. Once the allotted rinse time has elapsed, the stents are removed immediately and transferred to the second aqueous rinse, which is a beaker containing about 30 mls of purified water. This second aqueous rinse is also in the temperature range of about 60° to 75° C. The rinse time in the second aqueous rinse is again typically about 3¾ to 4¼ minutes. After the second rinse time has elapsed, the stents are removed and placed in vials filled with ethanol. After each run, the AHF solution should be replaced.

The embodiments discussed herein are in no way intended to limit the scope of the invention. Various changes and improvements may also be made to the invention without departing from the scope thereof.

What is claimed is:

1. A method of descaling a metallic device comprising a stent, the method comprising the steps of:
    placing the stent to be descaled in contact with a solution of ammonium hydrogen fluoride while applying ultrasonic energy to the solution to descale the stent, wherein the descaling removes slag material, burrs, sharp ends, or combinations thereof from a surface of the stent by dissolving metal atoms of the slag material, burrs, sharp ends, or combinations thereof into the ammonium hydrogen fluoride solution; and
    removing the stent from the solution and contacting the stent with a first aqueous rinse containing a nonionic surfactant while applying ultrasonic energy to the first rinse.

2. The method according to claim 1, wherein the solution is at a temperature in the range of about 60° C. to about 80° C.

3. The method according to claim 1, wherein the first aqueous rinse is at a temperature in the range of about 60° C. to about 80° C.

4. The method according to claim 1, wherein the solution contains about 3 to about 6 percent by volume of ammonium hydrogen fluoride.

5. The method according to claim 1, wherein the first aqueous rinse contains about 0.2 to about 1 percent by volume of the nonionic surfactant.

6. The method according to claim 5, wherein the nonionic surfactant comprises polyoxyethylene octyl phenyl ether of a formula $C_{14}H_{22}O(C_2H_4O)_n$ wherein the average of n per molecule is about 9 or 10.

7. The method according to claim 5, wherein the nonionic surfactant comprises sodium dodecylbenzenesulfonate.

8. The method according to claim 1, wherein the stent to be descaled is placed in contact with the solution of ammonium hydrogen fluoride for a period of time of less than about 12 minutes.

9. The method according to claim 8, wherein the period of time is in the range of about 7 minutes to about 10 minutes.

10. The method according to claim 1, wherein the stent is contacted with the first aqueous rinse for a period of about 4 minutes.

11. The method according to claim 1, wherein the stent comprises a triplex material comprising a layer of radiopaque material between layers of stainless steel.

12. The method according to claim 11, wherein the radiopaque material comprises titanium.

13. The method according to claim 1, further comprising electropolishing the surface of the stent after performing the step of descaling.

14. The method according to claim 1, wherein the solution of ammonium hydrogen fluoride further comprises nitric acid.

15. The method according to claim 1, further comprising removing the stent from the first rinse and contacting the stent with a second aqueous rinse while applying ultrasonic energy to the second rinse.

16. The method according to claim 15, wherein the second aqueous rinse contains about 0.4% by volume of a nonionic surfactant.

17. The method according to claim 15, wherein the second aqueous rinse contains about 1% by volume of a nonionic surfactant.

18. The method according to claim 15, wherein the second aqueous rinse consists of purified water.

19. The method according to claim 15, wherein the stent is contacted with the second aqueous rinse for a period of about 4 minutes.

20. The method according to claim 15, further comprising removing the stent from the second rinse and immersing the stent in a non-corrosive liquid.

21. The method according to claim 15, wherein the second aqueous rinse is at a temperature in the range of about 60° C. to about 80° C.

22. A method of descaling a metallic stent, comprising:
placing the stent to be descaled in contact with a solution of ammonium hydrogen fluoride while applying ultrasonic energy to the solution to descale the stent of slag material, burrs, sharp ends, or combinations thereof by dissolving metal atoms of the slag material, burrs, sharp ends, or combinations thereof into the ammonium hydrogen fluoride solution;
removing the stent from the solution and contacting the stent with an aqueous rinse containing a nonionic surfactant while applying ultrasonic energy to the rinse; and
electropolishing the stent after contacting the stent with the aqueous rinse.

23. The method according to claim 22, wherein the solution of ammonium hydrogen fluoride further comprises nitric acid.

24. A method of descaling a metallic stent comprising a triplex material comprising a layer of radiopaque material between layers of stainless steel, the method comprising the steps of:
placing the stent to be descaled in contact with a solution of ammonium hydrogen fluoride while applying ultrasonic energy to the solution to descale the stent, wherein the descaling removes slag material, burrs, sharp ends, or combinations thereof from a surface of the stent by dissolving metal atoms of the slag material, burrs, sharp ends, or combinations thereof into the ammonium hydrogen fluoride solution, the ammonium hydrogen fluoride solution dissolving metal of the stainless steel layers at approximately the same rate as metal of the radiopaque material layer so as to result in a substantially even profile across the triplex material after descaling; and
removing the stent from the solution and contacting the stent with an aqueous rinse containing a nonionic surfactant while applying ultrasonic energy to the rinse.

* * * * *